United States Patent
Todaka et al.

(10) Patent No.: US 7,278,027 B1
(45) Date of Patent: Oct. 2, 2007

(54) BIOMEDICAL RECOGNIZING SYSTEM COMPRISING IMAGE DIAGNOSIS WORKSTATION AND METHOD THEREFOR

(75) Inventors: Chiaki Todaka, Colorado, CO (US); Mitsuo Ohashi, Tokyo (JP); Ron Simpson, Colorado, CO (US); Toshihiko Furukawa, Colorado, CO (US)

(73) Assignee: Eizo Nanao Corporation, Ishikawa (JP)

( * ) Notice: Subject to any disclaimer, the term of this patent is extended or adjusted under 35 U.S.C. 154(b) by 611 days.

(21) Appl. No.: 10/432,708

(22) PCT Filed: Nov. 24, 2000

(86) PCT No.: PCT/JP00/08305

§ 371 (c)(1), (2), (4) Date: Sep. 15, 2003

(87) PCT Pub. No.: WO02/42964

PCT Pub. Date: May 30, 2002

(51) Int. Cl.
*H04K 1/00* (2006.01)
(52) U.S. Cl. .................... 713/186; 713/182; 382/115; 902/3
(58) Field of Classification Search ................ 713/186, 713/182; 382/115; 902/3; 705/2, 50
See application file for complete search history.

(56) References Cited

U.S. PATENT DOCUMENTS

| | | | | |
|---|---|---|---|---|
| 5,193,855 A | * | 3/1993 | Shamos | 283/117 |
| 5,272,760 A | * | 12/1993 | Echerer et al. | 382/132 |
| 6,094,589 A | * | 7/2000 | Schmitt | 600/407 |
| 6,219,439 B1 | * | 4/2001 | Burger | 382/115 |
| 6,226,398 B1 | * | 5/2001 | O'Neill et al. | 382/162 |
| 6,256,737 B1 | * | 7/2001 | Bianco et al. | 713/186 |
| 2001/0036300 A1 | * | 11/2001 | Xia et al. | 382/125 |
| 2002/0010679 A1 | * | 1/2002 | Felsher | 705/51 |
| 2002/0035484 A1 | * | 3/2002 | McCormick | 705/2 |

FOREIGN PATENT DOCUMENTS

JP 04321096 A * 11/1992

* cited by examiner

*Primary Examiner*—Kim Vu
*Assistant Examiner*—April Y. Shan
(74) *Attorney, Agent, or Firm*—Muirhead and Saturnelli, LLC

(57) ABSTRACT

A biomedical recognition system includes diagnostic image information obtained by taking an image of a patient, a workstation storing the diagnostic image information, and a display device for displaying the diagnostic image information. A sensor is provided for capturing a biomedical information of a doctor. A biomedical information recognition system is connected to the sensor and integrated in the workstation for comparing a previously registered biomedical information and the biomedical information captured by the sensor. A display device control system is provided for causing the display device to display a diagnostic image linked to the biomedical information if a comparing result indicates a correspondence between the previously registered biomedical information and the biomedical information captured by the sensor, and for causing the display device to discontinue a part of functions thereof if the comparing result indicates a non-correspondence between the information.

15 Claims, 3 Drawing Sheets

(a)

(b)

BIOMEDICAL RECOGNIZING SYSTEM COMPRISING IMAGE DIAGNOSIS WORKSTATION AND METHOD THEREFOR

TECHNICAL FIELD

The present invention relates to a diagnostic image information obtained through a radiography of patient, and a workstation storing the diagnostic image information as well as a display for displaying the diagnostic image information.

BACKGROUND OF THE ART

In the past few years, a CRT image diagnosis using a CRT monitor has been becoming active in the United States of America and the European countries. In 2000, a percentage of spread thereof in the world market is approximately 5 percent to 8 percent. In eight years from now, about 70 percent of the spread may be estimated. The CRT image diagnosis uses any displays utilizing an electrical display system instead of the conventional diagnostic X-ray film. A diagnostic display monitor as electrical display is in contrast to the X-ray film in view of the following. For an input device, a data storage device and a CRT image diagnosis device, there is needed information about when those devices were manufactured, and further information about performances and conditions of those devices, for example, values of brightness, gamma-characteristics and MTF, and furthermore information about who and when made measurements and moreover information about who and when made judgements, and what images were used for making the judgements, because the information allow the security of medical doctors who diagnose, and the certification of the patient. Also, the information is extremely effective in lawsuits between the medical doctors and the patient in view of the diagnosis.

In the present circumstances, if the image appears on the film, then the medical doctor, who diagnoses, puts his or her signs or markings thereon. If the image is displayed on the CRT, then an identification of an individual is made by entry of a pass-word from a key board.

In the present circumstances, there has been used no effective method of specifying an operator or an individual. When the medical doctor becomes apart from the diagnostic image, then a security problem may be caused. The entry of a password each time for keeping the security is not efficient. As shown in FIG. 3(a), the present system has utilized a method of making the medical doctor, who intends to diagnose, enter the password, diagnostic information, and individual information, for which reason there have been a problem with the complication of data entry and another problem with a poor security protected by only the password. The largest problem at the present circumstances is that the image for diagnosis is in such a passive state as to allow anyone to view the diagnostic image on the CRT.

FIG. 3(b) shows that a diagnostic medical doctor enters only the diagnostic information into an information instrument, and the information instrument collects itself biomedical informations for automatic transmission of the biomedical information into the information instrument in the simple presence of the medical doctor, thereby solving the problems with the security and the complication.

In a picture archiving communication system (disclosed in Japanese laid-open patent publication No. 8-161461), an identification number of an image is managed to allow an interpreting medical doctor to interpret an image of the patient, whom the interpreting medical doctor is in charge of, through a predetermined workstation. In this system, the identification is made based on the name or the identification number of the interpreting medical doctor, whereby any persons, who has known the name or the identification number of the interpreting medical doctor, are permitted to interpret.

In a method and an apparatus for certifying an individual (disclosed in Japanese laid-open patent publication No. 2000-268175), certification condition data, which specify at least one biomedical feature for the individual certification, are stored in an IC card 200 carried by a user, so that a detection is made, from the user, of a biomedical feature which corresponds to the certification condition data read out of this IC card 200, thereby achieving the individual certification. Particularly, there are disclosed a fingerprint certification algorithm, a voiceprint certification algorithm and a face certification algorithm. There is not disclosed effects in security and data management by application of this certification method to reading out the medical image.

It is desirable to make an objective CRT-diagnostic image active to permit only a designated individual to view the image.

SUMMARY OF THE INVENTION

A biomedical recognition system of the present invention includes a diagnostic image information obtained by taking an image of a patient, a workstation storing the diagnostic image information, and a display device for displaying the diagnostic image information, wherein the workstation is a CRT image diagnostic workstation which comprises: a sensor provided to the display device for capturing biomedical information of a doctor which is present in front of the display device; a biomedical information recognition means being connected to the sensor and also being integrated in the workstation for comparing a previously registered biomedical information and the biomedical information by the sensor; and a display device control means for causing the display device to display a diagnostic image linked to the biomedical information if comparing result is a correspondence between the previously registered biomedical information and the biomedical information captured by the sensor, and for causing the display device to discontinue a part of functions thereof if the comparing result is a non-correspondence between the information.

The sensor for capturing the biomedical information comprises at least one of an image input device, a voice input device, a fingerprint identification device, and an iris-scanner and a face-scanner.

The diagnostic image comprises at least one of an X-ray image, a CI-image, an MRI-image, and a CR-image.

The biomedical information is linked to an individual information.

The diagnostic image is linked to a manufacturing information of the display device, a performance information thereof, or a situational information thereof.

If a result of the comparison by the biomedical information recognition means is the non-correspondence between the biomedical informations, then an illegal access result is recorded.

A biomedical recognition method of the present invention utilizes a diagnostic image information obtained by taking an image of a patient, a workstation, storing the diagnostic image information, and a display device for displaying the diagnostic image information, and the workstation being a CRT image diagnostic workstation. The method comprises the steps of: capturing a biomedical information of an object, which is present in front of the display device, by a sensor provided to the display device; comparing a previously registered biomedical information and an obtained biomedical information; and causing the display device to display a diagnostic image linked to the biomedical information if a comparing result is a correspondence between those informations, and causing the display device to discontinue a part of functions thereof if the comparing result is a non-correspondence between those informations.

The step of capturing the biomedical information by the sensor uses at least one of an image input device, a voice input device, a fingerprint identification device, and an iris-scanner and a face-scanner.

The diagnostic image comprises at least one of an X-ray image, a CI-image, an MRI-image, and a CR-image.

The biological biomedical information is linked to an individual information.

The diagnostic image is linked to a manufacturing information of the display device, a performance information thereof, or a situational information thereof.

If a result of the comparison by the biomedical information recognition means is the non-correspondence between the biomedical informations, then an illegal access result is recorded.

BRIEF DESCRIPTIONS OF DRAWINGS

DETAILED DESCRIPTION OF VARIOUS EMBODIMENTS

The present invention will be described in details with reference to the accompanying drawings.

Figure 1:
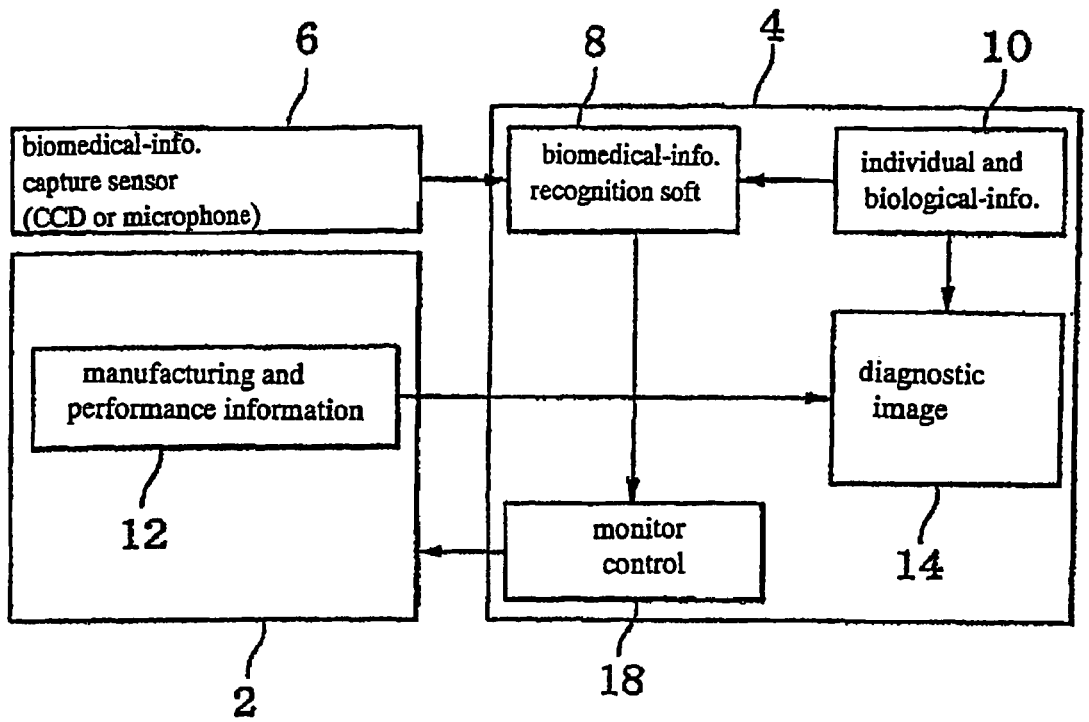
FIG. 1 is a block diagram illustrative of an embodiment of a biomedical recognition system with a CRT image diagnostic workstation in accordance with the present invention.

FIG. 1 is a block diagram illustrative of an embodiment of a biomedical recognition system with a CRT image diagnostic workstation in accordance with the present invention. A biomedical recognition system comprises a CRT monitor 2, a workstation 4 connected to the CRT monitor 2, and a sensor connected to the workstation 4 for capturing biomedical informations.

The CRT monitor 2 is a monitor of the workstation 4 for displaying a medical image 14. An image display device is not limited to the CRT. Any computer displays for displaying an image are available such as liquid crystal displays, plasma displays, and EL-displays.

The CRT monitor 2 stores and sends, to the workstation 4, manufacturing information including manufacturing dates, manufacturing numbers, manufacturing places, and performance information 12 including variations over times such as brightness, gamma-characteristic and MTF.

The workstation 4 comprises a biomedical information recognition software 8 coupled to a sensor 6 capturing biomedical informations therein, individual and biomedical informations 10 coupled to the biomedical information recognition software 8, diagnostic image data 14 linked to the individual and biomedical informations 10, and a monitor control unit 18 coupled to the biomedical information recognition software 8.

The biomedical information recognition software 8 receives a face-identification information, a fingerprint-identification information, and a voiceprint-identification information from the biomedical information capturing sensor 6. The biomedical information recognition software 8 retrieves a previously registered biomedical information which comprises a previously registered face-identification information, a previously registered fingerprint-identification information, and a previously registered voiceprint-identification information which are previously registered in the individual and biomedical informations 10, on the basis of characteristic informations of the received face-identification information, the received fingerprint-identification information, and the received voiceprint-identification information. If the informations retrieved by the biomedical information recognition software 8 correspond to the received informations, then a registered individual information corresponding to the registered biomedical information is fetched. A notice of the correspondence to the biomedical information is recorded in a memory in the workstation 4 (not illustrated). The biomedical information recognition software 8 also transmits the notice of the correspondence to the biomedical information to the monitor control unit 18.

If the informations retrieved by the biomedical information recognition software 8 do not correspond to the received informations, then the biomedical information recognition software 8 stores another notice of the non-correspondence to the biomedical information in the memory in the workstation 4 (not illustrated).

The individual and biomedical informations 10 are previously registered which include face-image data of one or more medical doctors who utilize the present system in a front view, a left view, a right view and a left-front perspective view, and a right-front perspective view, as well as finger-print captured informations and voice-print informations. Upon receipt of an inquiry from the biomedical information recognition software 8, the individual and biomedical informations 10 provides an information related thereto.

The diagnostic image data 14 are data including any patient image of an X-ray image, a CT-image, an MRI-image, and a CR-image. As a secondary information of the diagnostic image data 14, there are recorded, in the diagnostic image, a patient name, a date of taking the image, an information of a site at which the image is taken, and an information of a medical doctor in charge of this patient, as well as manufacturing and performance information of the image display device when the image information is inspected.

If the monitor control unit 18 receives a signal to the effect of the correspondence with the registered information as retrieved by the biomedical information recognition software 8, then the monitor control unit 18 releases the display device from a locked-state, and allows the display device to display a diagnostic image of the patient, of which the medical doctor is in charge. If the monitor control unit 18 receives another signal to the effect of the non-correspondence with the registered information as retrieved, then the monitor control unit 18 sill keeps the display device in the locked-state.

The biomedical information capturing sensor 6 comprises an image input device, a voice input device, and a finger-print-identification device, and optionally may further include an iris-scanner and a face-scanner. Biometrics informations such as faces, body forms, and the ways of walks are captured through the image input device and recorded on the individual and biomedical informations 10. Also, another information which characterizes the medical doctor such as the voice-print is recognized as a voice information and captured through the voice input device such as a microphone, whereby the captured information is recorded on the individual and biomedical informations 10. A fingerprint of the medical doctor is captured by the fingerprint-identification device and then recorded on the individual and biomedical informations 10.

Figure 2:
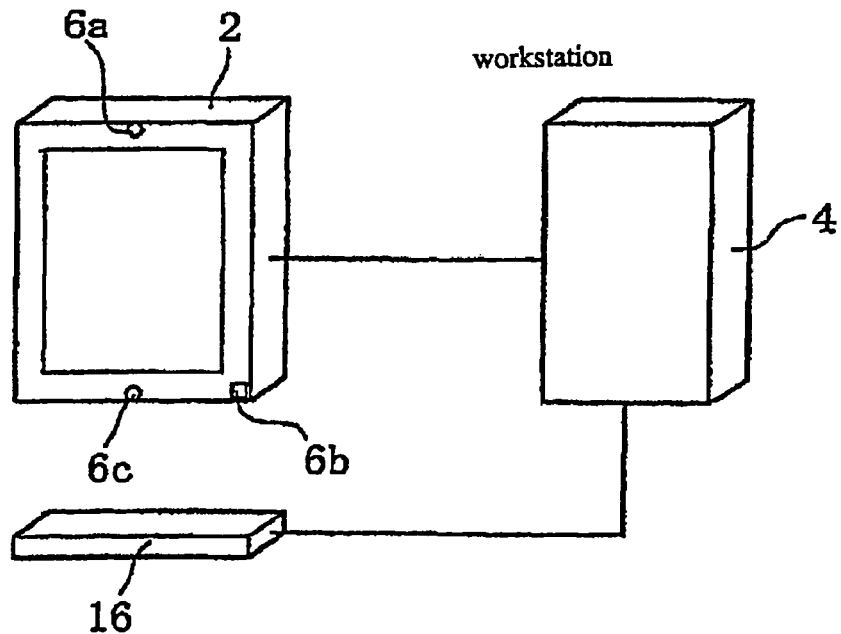
FIG. 2 is a block diagram illustrative of another embodiment of a biomedical recognition system with a CRT image diagnostic workstation in accordance with the present invention.
Figure 3:
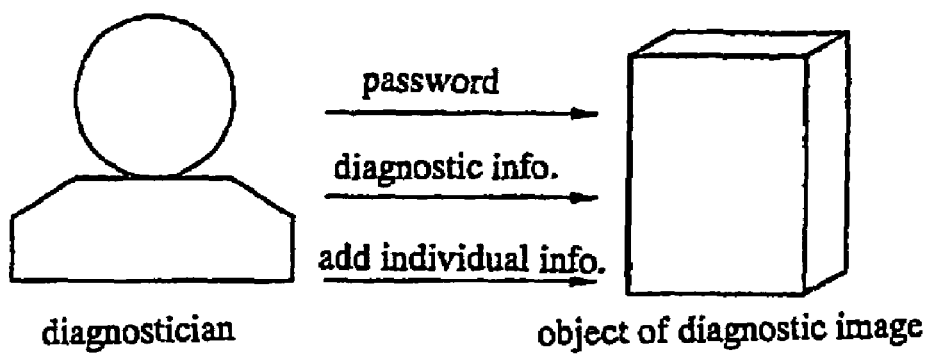
FIG. 3 is conceptional views of a conventional system and a system of the present invention.
Figure 3:
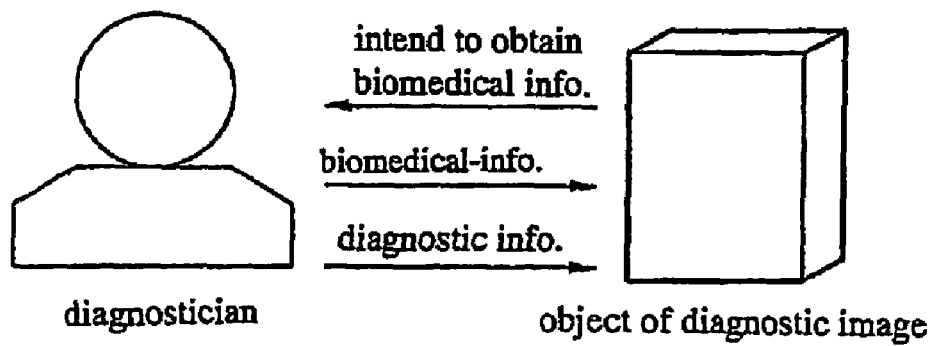

FIG. 2 is a schematic view of one embodiment of a biomedical recognition system with the CRT image diagnostic workstation in accordance with the present invention. The biomedical recognition system comprises a CRT monitor 2, a workstation 4 connected to the CRT monitor 2, a key-board-mouth 16 connected to the workstation 4. An image input device 6a, a voice input device 6c and a fingerprint-identification device 6b are placed over the CRT monitor 2.

The image input device 6a is placed at a front top of the CRT monitor 2 for capturing, from an upper side, a face-information of a person in front of the CRT monitor 2.

The voice input device 6c is placed at a front bottom of the CRT monitor 2 for positioning it at the same level of a mouth of the person in front of the CRT monitor 2.

The fingerprint-identification device 6b is also placed at the front bottom of the CRT monitor 2 for positioning it for a suitable placement of a finger of the person in front of the CRT monitor 2. Those positions are one examples but should not be limitative.

Figure 4:
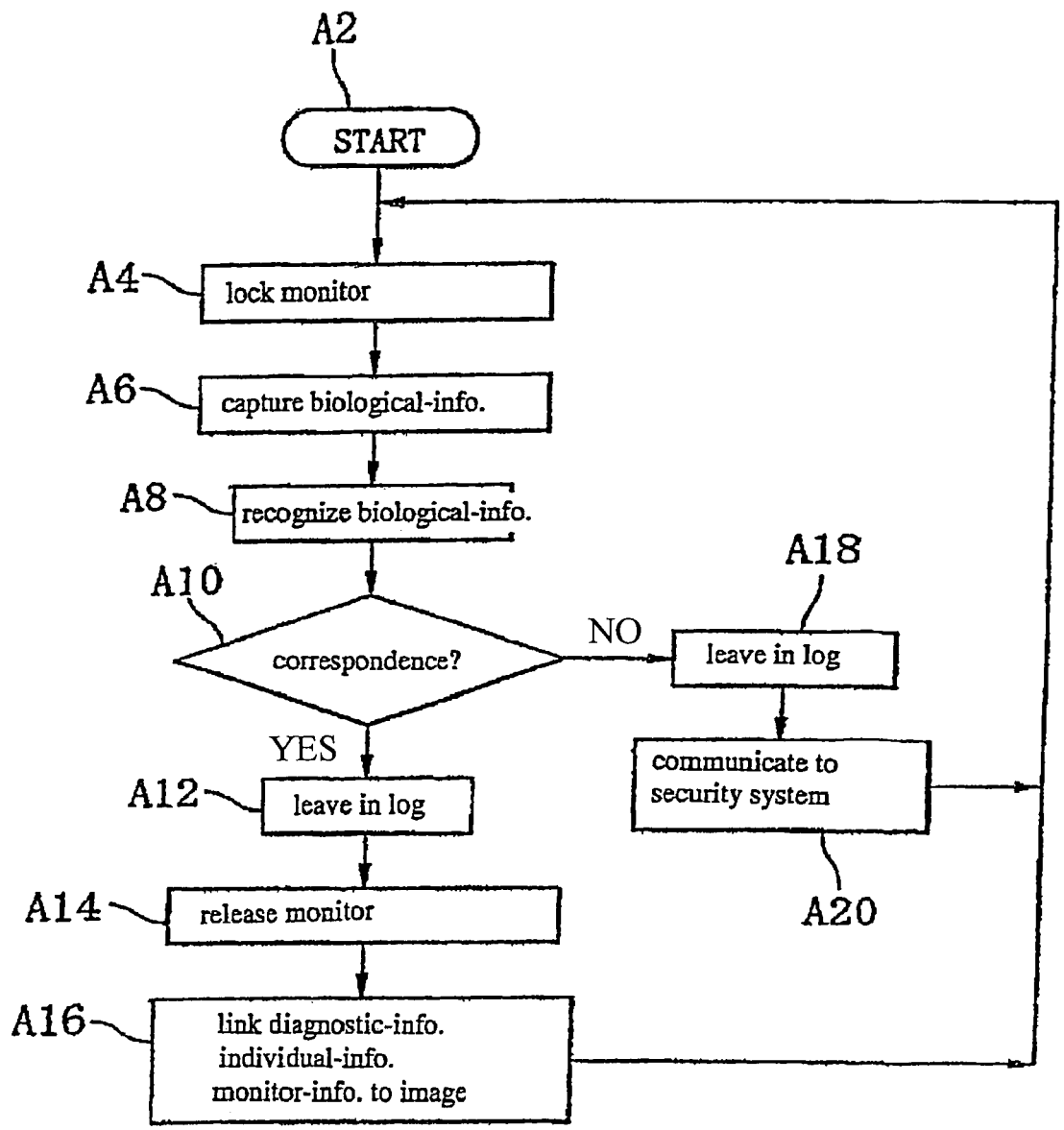
FIG. 4 is a flow chart illustrative of a biomedical recognition method with a CRT image diagnostic workstation in accordance with the present invention.

FIG. 4 is a block diagram showing the biomedical recognition system with the CRT image diagnostic workstation in accordance with the present invention.

After start (A2), the monitor control unit 18 places the monitor 2 of the CRT image diagnostic workstation 4 in a locked-state (A4) for inhibiting any illegal use.

A collection of the biomedical informations is always continued. A medical doctor takes a seat in front of the monitor 2, so as to allow that the image input device 6a takes an image of a face of the medical doctor, and the voice input device 6c collects and takes a voice of the medical doctor, and the finger of the medical doctor is placed on the fingerprint-identification device 6b for identifying the fingerprint, whereby the biomedical informations of the medical doctor are captured (6A).

The biomedical information recognition software 8 recognizes the face-information, the voice-information and the fingerprint information and compares them with the registered individual and biomedical informations 10 (A10).

If a correspondence with the registered person is confirmed, then the information is recorded in a memory of the workstation 4 (A12) before the monitor control 18 releases the monitor 2 from the locked-state (A14).

Further, a diagnostic information of the patient, of which the medical doctor is in charge, and the individual information and the further information related to the monitor 2 are coupled to the diagnostic image (A16).

If no correspondence with the registered person is confirmed, then the information is recorded in a memory of the workstation 4 (A18) before the monitor control unit 18 keeps the monitor 2 in the locked-state and communicates with the security system (A20).

INDUSTRIAL APPLICABILITY

As described above, the biomedical information recognition system with the CRT image diagnostic workstation in accordance with the present invention is free of any complication of input of pass-word, and prevents any deterioration of security even if the pass-ward is stolen, but protects the diagnostic informations with the perfect security depending upon the biometrics informations possessed by the person himself or herself.

The recognition of the biomedical information allows displaying only patient data necessary for the medical doctor based on the linked-informations, thereby curtailing operations of again retrievals of the patient diagnostic informations from the information instruments.

Further, the diagnostic information is linked to a situational problem, for which reason the use of the present system for diagnosis allows the situational information of the diagnosis to be recorded which is available as a roof or an evidence for a medical law suit.

What is claimed is:

1. A biomedical recognition system, comprising:
   a workstation for storing diagnostic image information obtained by taking an image of a patient; and
   a display device for displaying the diagnostic image information,
   wherein said workstation is an image diagnostic workstation which includes:
   a sensor for capturing biomedical information of a doctor;
   a biomedical information recognition means connected to said sensor and integrated in said workstation for comparing previously registered biomedical information and the biomedical information captured by the sensor; and
   a display device control means for causing said display device to display a diagnostic image linked to the biomedical information captured by the sensor if a comparing result indicates a correspondence between the previously registered biomedical information and the biomedical information captured by the sensor, and for causing said display device to discontinue a part of functions thereof if said comparing result indicates a non-correspondence between the previously registered biomedical information and the biomedical information captured by the sensor, and
   wherein said diagnostic image is linked to additional information including manufacturing information of said display device, performance information thereof, or situational information thereof recorded when the diagnostic image information is inspected, the additional information corresponding to a condition of the display device and being recorded in the diagnostic image.

2. The biomedical recognition system as claimed in claim 1, wherein said sensor for capturing said biomedical information comprises at least one of an image input device, a voice input device, a fingerprint identification device, an iris-scanner and a face-scanner.

3. The biomedical recognition system as claimed in claim 1 or 2, wherein said diagnostic image comprises at least one of an X-ray image, a CT-image, an MRI-image, and a CR-image.

4. The biomedical recognition system as claimed in any one of claims 1 and 2, wherein said diagnostic image is further linked to individual information.

5. The biomedical recognition system as claimed in any one of claims 1 and 2, wherein if the comparison result of said comparison by said biomedical information recognition means indicates the non-correspondence between the previously registered biomedical information and the biomedical information captured by the sensor, then an illegal access result is recorded.

6. A biomedical recognition method utilizing diagnostic image information obtained by taking an image of a patient, said method comprising the steps of:
    storing the diagnostic image information on a workstation, said workstation being an image diagnostic workstation;
    displaying the diagnostic image information on a display device;
    capturing biomedical information of a doctor by a sensor;
    comparing previously registered biomedical information and the biomedical information captured by the sensor; and
    causing said display device to display a diagnostic image linked to the biomedical information captured by the sensor if a comparing result indicates a correspondence between the previously registered biomedical information and the biomedical information captured by the sensor, and causing said display device to discontinue a part of functions thereof if said comparing result indicates a non-correspondence between the previously registered biomedical information and the biomedical information captured by the sensor, and
    wherein said diagnostic image is linked to additional information including manufacturing information of said display device, performance information thereof, or situational information thereof recorded when the diagnostic image information is inspected, the additional information corresponding to a condition of the display device and being recorded in the diagnostic image.

7. The biomedical recognition method as claimed in claim 6, wherein said step of capturing said biomedical information by said sensor uses at least one of an image input device, a voice input device, a fingerprint identification device, an iris-scanner and a face-scanner.

8. The biomedical recognition method as claimed in claim 6 or 7, wherein said diagnostic image comprises at least one of an X-ray image, a CT-image, an MRI-image, and a CR-image.

9. The biomedical recognition method as claimed in any one of claims 6 and 7, wherein said diagnostic image is further linked to individual information.

10. The biomedical recognition method as claimed in any one of claims 6 and 7, wherein if a result of said comparison by said biomedical information recognition means is the non-correspondence between the previously registered biomedical information and the biomedical information captured by the sensor, then an illegal access result is recorded.

11. The biomedical recognition method as claimed in claim 8, wherein said diagnostic image is further linked to individual information.

12. The biomedical recognition method as claimed in claim 6,
    wherein said sensor for capturing said biomedical information comprises at least one of an image input device, a voice input device, a fingerprint identification device, an iris-scanner and a face-scanner;
    wherein said diagnostic image comprises at least one of an X-ray image, a CT-image, an MRI-image, and a CR-image;
    wherein said diagnostic image is further linked to individual information; and
    wherein if the comparing result of said comparison by said biomedical information recognition means indicates the non-correspondence between the previously registered biomedical information and the biomedical information captured by the sensor, then an illegal access result is recorded.

13. The biomedical recognition system as claimed in claim 3 wherein said diagnostic image is further linked to individual information.

14. The biomedical recognition system as claimed in claim 1,
    wherein said sensor for capturing said biomedical information comprises at least one of an image input device, a voice input device, a fingerprint identification device, an iris-scanner and a face-scanner;
    wherein said diagnostic image comprises at least one of an X-ray image, a CT-image, an MRI-image, and a CR-image;
    wherein said biomedical information is linked to individual information; and
    wherein if the comparing result of said comparison by said biomedical information recognition means indicates the non-correspondence between the previously registered biomedical information and the biomedical information captured by the sensor, then an illegal access result is recorded.

15. A biomedical recognition system, comprising:
    a display device for displaying diagnostic image information;
    a sensor connected to said display device for capturing biomedical information;
    executable code that receives said biomedical information captured by said sensor and compares said biomedical information captured by the sensor with previously registered biomedical information;
    executable code that controls display of a diagnostic image linked to the biomedical information captured by the sensor if said biomedical information captured by the sensor corresponds to said previously registered biomedical information, and discontinues a part of functions of said display device if said captured biomedical information does not correspond with said previously registered biomedical information, wherein said diagnostic image is linked to additional information including manufacturing information of said display device, performance information thereof, or situational information thereof recorded when the diagnostic image information is inspected, the additional information corresponding to a condition of the display device and being recorded in the diagnostic image.

* * * * *